(12) United States Patent
Schoepp

(10) Patent No.: US 8,657,809 B2
(45) Date of Patent: Feb. 25, 2014

(54) SURGICAL NAVIGATION SYSTEM

(75) Inventor: Hans Schoepp, Freiburg (DE)

(73) Assignee: Stryker Leibinger GmbH & Co., KG, Freiburg (DE)

(*) Notice: Subject to any disclaimer, the term of this patent is extended or adjusted under 35 U.S.C. 154(b) by 1 day.

(21) Appl. No.: 12/893,821

(22) Filed: Sep. 29, 2010

(65) Prior Publication Data
US 2012/0078236 A1    Mar. 29, 2012

(51) Int. Cl.
A61B 19/00    (2006.01)

(52) U.S. Cl.
USPC ............ 606/1; 600/424; 600/425; 600/426; 600/427

(58) Field of Classification Search
USPC .................................. 600/424–427; 606/1
See application file for complete search history.

(56) References Cited

U.S. PATENT DOCUMENTS

| | | | |
|---|---|---|---|
| 5,583,343 A * | 12/1996 | Dilmanian et al. | 250/475.2 |
| 5,617,857 A | 4/1997 | Chader et al. | |
| 5,622,170 A | 4/1997 | Schulz | |
| 5,694,142 A | 12/1997 | Dumoulin et al. | |
| 5,704,897 A | 1/1998 | Truppe | |
| 5,792,147 A | 8/1998 | Evans et al. | |
| 5,795,294 A | 8/1998 | Luber et al. | |
| 5,848,967 A | 12/1998 | Cosman | |
| 6,246,900 B1 | 6/2001 | Cosman et al. | |
| 6,282,437 B1 | 8/2001 | Franck et al. | |
| 6,497,134 B1 | 12/2002 | Faul et al. | |
| 6,529,765 B1 * | 3/2003 | Franck et al. | 600/427 |
| 6,608,688 B1 | 8/2003 | Faul et al. | |
| 6,978,167 B2 | 12/2005 | Dekel et al. | |
| 7,231,063 B2 | 6/2007 | Naimark et al. | |
| 7,725,162 B2 | 5/2010 | Malackowski et al. | |
| 2004/0138556 A1 * | 7/2004 | Cosman | 600/424 |
| 2006/0176242 A1 | 8/2006 | Jaramaz et al. | |
| 2007/0018975 A1 | 1/2007 | Chuanggui et al. | |
| 2007/0038059 A1 | 2/2007 | Sheffer et al. | |
| 2007/0238981 A1 | 10/2007 | Zhu et al. | |
| 2008/0208041 A1 | 8/2008 | Gilboa | |

FOREIGN PATENT DOCUMENTS

DE    69503814    12/1998

(Continued)

OTHER PUBLICATIONS

"Stereoscopic Augmented Reality System for Computer Assisted Surgery", Liévin et al., CARS 2001, Berlin, Germany, Jun. 27-30, 2001, 5 pages.

"Intuitive and Lightweight User Interaction for Medical Augmented Reality", Fischer et al., VMV 2005, Erlangen, Germany, Nov. 16-18, 2005, 9 pages.

(Continued)

Primary Examiner — Bill Thomson
Assistant Examiner — Jeffrey Lipitz
(74) Attorney, Agent, or Firm — Howard & Howard Attorneys PLLC

(57) ABSTRACT

A surgical navigation system is disclosed including a camera that is fixedly attached to a patient. The camera space merges with the patient space and thereby eliminates the need for a separate patient tracker. The surgical navigation system calculates the position of a surgical tool with a tracking device in view of the camera and shows on a display device the position of the surgical tool with respect to the patient superimposed and in correlation with a scan image of the patient.

26 Claims, 6 Drawing Sheets

(56) References Cited

FOREIGN PATENT DOCUMENTS

| | | |
|---|---|---|
| DE | 10238011 A1 | 3/2004 |
| DE | 102005058240 A1 | 6/2007 |
| EP | 1470791 A1 | 10/2004 |
| WO | WO99/38449 A1 | 8/1999 |
| WO | WO2004/075768 A2 | 9/2004 |
| WO | WO2005/091220 A1 | 9/2005 |
| WO | WO2007/065750 A1 | 6/2007 |
| WO | WO2008/036050 A2 | 3/2008 |
| WO | WO2008/036050 A3 | 3/2008 |

OTHER PUBLICATIONS

"Augmented Reality in Surgery", James C. Thomas, Studentbmj, vol. 16, Mar. 2008, pp. 108-109.
"Augmented Reality in Surgical Procedures", Samset et al., Proceedings of SPIE 2008;6806, 12 pages.
"ActiSight. Precisely What You've Been Waiting For", ActiViews, Inc., 2008, 2 pages.
European Search Report dated Jan. 16, 2012, for EP Application No. 11004809.7-1269, 6 pages.
Reply dated Jul. 12, 2012, 18 pages, to a European Search Report of Jan. 16, 2012 for EP Application No. 11004809.7-1269.

\* cited by examiner

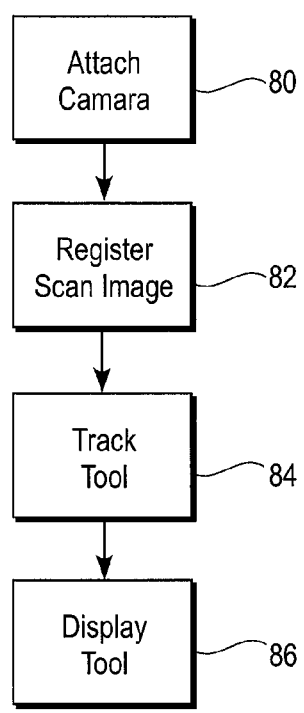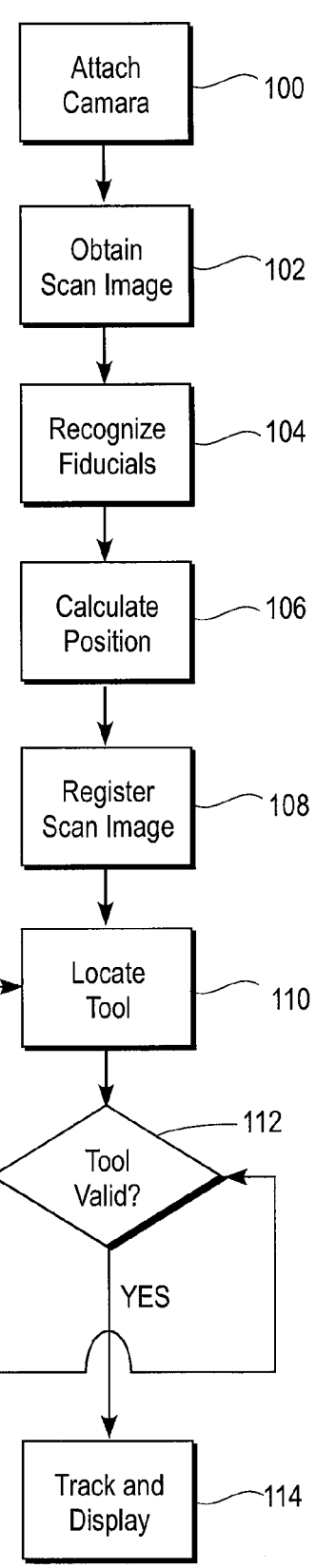

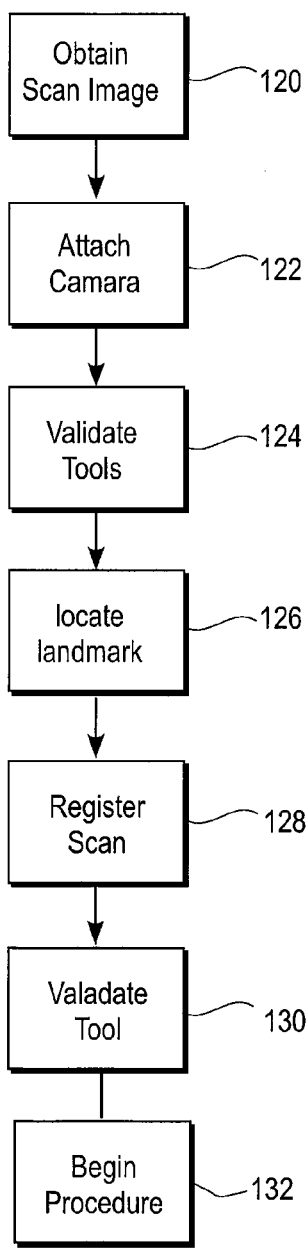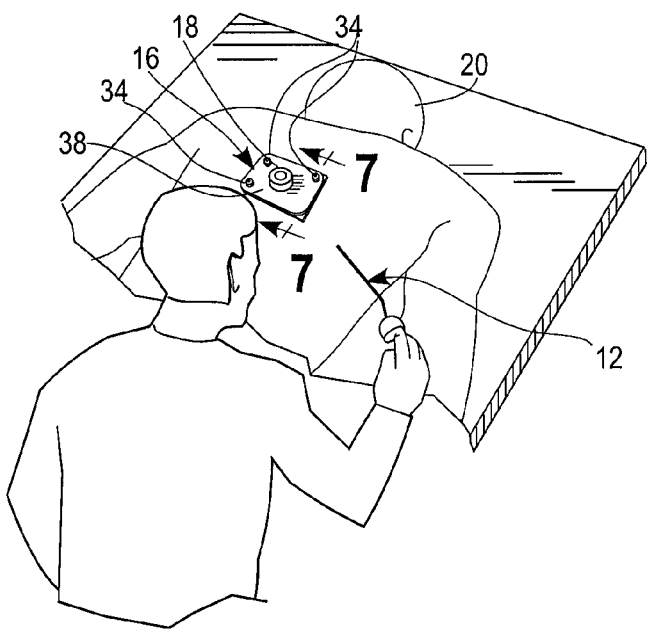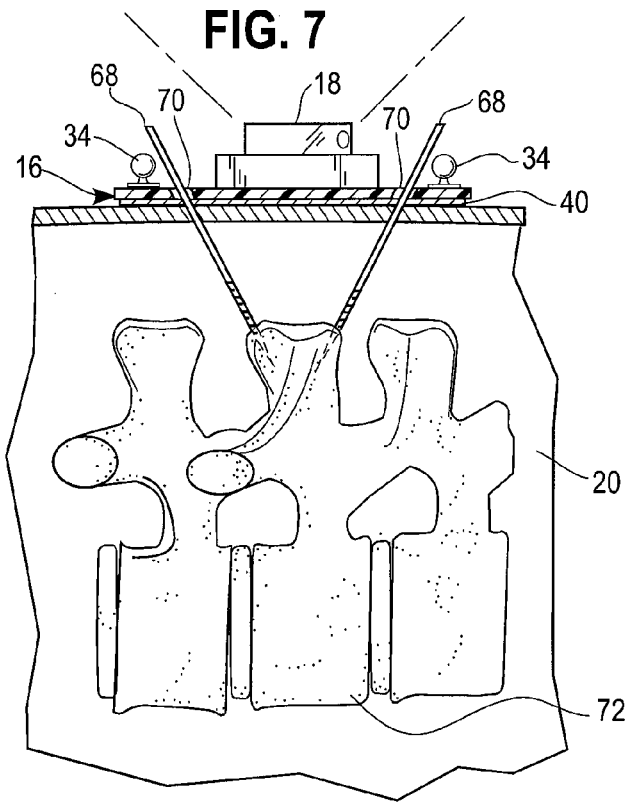

SURGICAL NAVIGATION SYSTEM

BACKGROUND

1. Field of the Invention

The present invention relates to computer implemented navigation systems used in surgical procedures.

2. Background of the Invention

Computerized surgical navigation systems are used to help guide a surgeon operating on a patient. In many instances, the use of navigation systems enables the surgeon to perform a surgery on a patient in a minimally invasive manner. For example, a navigation system helps the surgeon visualize or see the location of a surgical tool in relation to portions of the body that are not directly visible to the surgeon, such as organs or bones on the inside of the body, by showing on a display apparatus such as a television monitor or computer monitor the position of the surgical tool in relation to the portion inside the body. Thus, smaller and/or fewer incisions into the body are needed because the surgeon does not need a direct visual line of sight to a location of interest inside the body. Surgical navigation systems may also be used in other types of surgery, such as an orthopedic procedure, to help guide the surgeon while making cuts and/or placing objects on the patient's bones, for example, in positions that have been planned and marked with respect to pre-operative images taken of the body but without having to directly mark such locations on the patient's body.

There are many types of navigation systems that have been developed to assist with surgical procedures. In one well known exemplary navigation system, a multi-camera navigation system in communication with a computer processor tracks tracking devices with LED's that flash and have a known spatial configuration. One or more tracking devices called tool trackers are attached to surgical tools in a known spatial configuration, and such information is located in a database available to the computer processor. One or more tracking devices called patient trackers are also attached in a fixed position to the patient, such as with pins inserted into a bone. A set of two, three, or more tracking cameras, such as charge-coupled device (CCD) cameras, are located within an operating room and are connected to the computer processor. The CCD cameras are positioned in a known, fixed relation with each other, such as on a single bar, so that images from each of the three cameras may be processed and combined to triangulate the position of the trackers as viewed by the CCD cameras. In this system, the computer processor is used to concatenate several different position vectors including positional vectors from the cameras to the tool trackers and positional vectors from the cameras to the patient trackers to track the position of surgical tools with respect to the body. With appropriate registration of various coordinate systems performed by the computer processor, the position of the tool may then be shown on a display monitor in registration with a scan image of the patient, such as an X-ray, ultra-sound, MRI, or CT scan image or the like, that shows various points of interest on the inside of the body. Although such navigation systems are highly effective in helping the surgeon navigate a tool inside the body without being able to see directly into the body, this system takes a large amount of computing resources in order to make the required mathematical transformations of the various positional vectors from the cameras to the tool trackers and the cameras to the patient trackers. Although ongoing improvement in computing technology reduces the amount of time necessary to make such calculations, because the navigation is performed in real time during the surgery, any increase in the speed of calculation such as by reducing the amount of computing resources necessary would be desirable. Some exemplary surgical navigation systems based generally on this type of technology are disclosed in Chader U.S. Pat. No. 5,617,857, Schulz U.S. Pat. No. 5,622,170, Faul et al. U.S. Pat. No. 6,497,134, Faul et al. U.S. Pat. No. 6,608,688, and Malackowski et al. U.S. Pat. No. 7,725,162, each of which is incorporated in its entirety herein.

Another type of surgical navigation system includes a navigation camera is attached directly to a surgical tool for insertion into a patient's body. A target patch with optical navigation markers, printed thereon, is placed on the patient's body at or near a desired point of entry into the body. The patch is registered with the body, and the camera views the patch as the surgical tool is inserted into the patient's body. The camera is connected to a computer processor, which is programmed to process images of the optical navigation markers from the camera to determine a position of the surgical tool in reference to the patch and, thereby, the patient's body. Thus, the computer processor is able to process the images of the patch with the navigation markers thereon taken by the camera to track the position of, for example, a tip of the surgical tool that has been inserted in the body subcutaneously and displays such position on a computer monitor in registration with a scan image of the area of interest. An example of such a system is disclosed in more detail in Gilboa U.S. Patent Application Publication No. 2008/0208041, which is incorporated herein in its entirety. Although useful for navigating the surgical tool, this surgical navigation system requires that each surgical tool has its own tracking camera attached thereto and/or tracking patch for attachment to the patient's body that has been adapted specifically for a particular use with a particular surgical instrument and/or procedure. In addition, having a camera placed on the surgical tool itself may be cumbersome to the surgeon by adding weight or wires thereto.

Thus, the inventor of the present invention believes that it would be advantageous to overcome one or more of the challenges of these prior art navigation systems, such as reducing the amount of computing resources necessary to track the position of the tool tracker with respect to the patient's body and show such position in registration with a scan image of the body, removing cumbersome objects such as cameras from surgical tools, and providing a single system that may be readily and easily adaptable for use with many different instruments and procedures.

SUMMARY OF THE INVENTION

In one aspect of the invention, a surgical navigation system comprises a camera including means for attaching the camera in a fixed position to a patient, a surgical tool including a tracking element readable by the camera, and a computer processing unit comprising means for recognizing the tracking element in an image obtained by the camera and means for tracking the position of the surgical tool. A communication link is adapted to transmit images from the camera to the computerized processing unit.

In another aspect of the invention, a surgical navigation camera comprises a camera having a known focus, and means for attaching the camera in a fixed position to a patient.

In a further aspect of the invention, a method of tracking a surgical tool with respect to a patient comprises the steps of attaching a camera to the patient in a fixed position, and tracking a position of the surgical tool in relation to the patient using pictures taken by the camera and a computerized navigation system.

Other aspects and advantages of the present invention will become apparent upon consideration of the following detailed description.

BRIEF DESCRIPTION OF THE DRAWINGS

FIG. 3 is a flow chart of one method of using the surgical navigation system;

FIG. 4 is a flow chart of a method of using the surgical navigation system with an automatic registration procedure;

FIG. 5 is a flow chart of a method of using the surgical navigation system with a manual registration procedure; and FIGS. 6 and 7 show the surgical navigation system as used in a different surgical procedure and with another attachment mechanism for a navigation camera.

DETAILED DESCRIPTION

Figure 1:
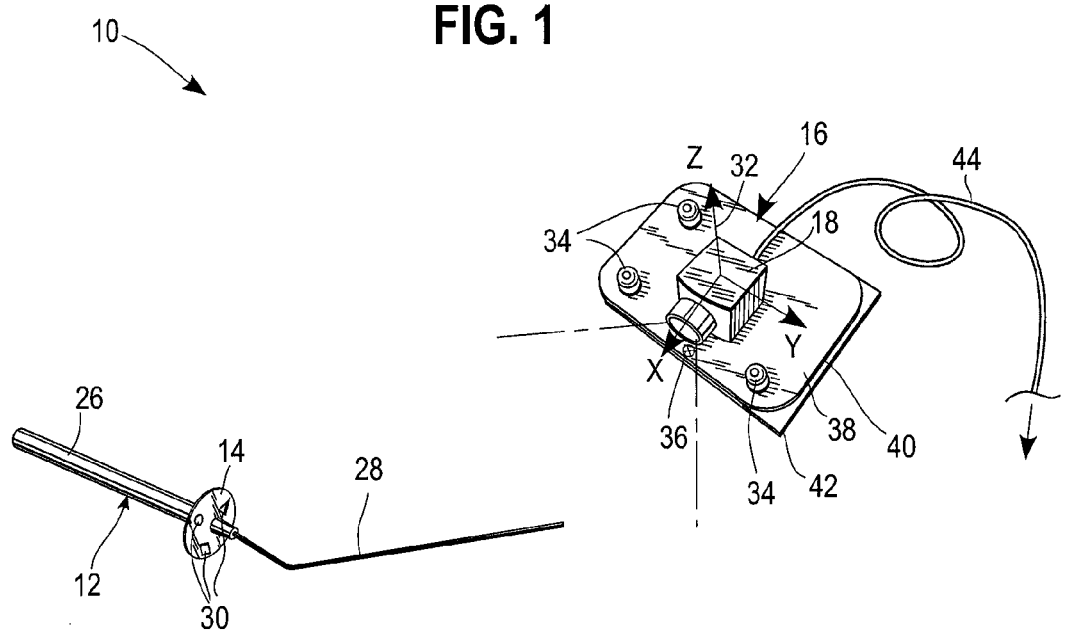
FIG. 1 is a diagrammatic depiction of a surgical navigation system according to the invention.
Figure 2:
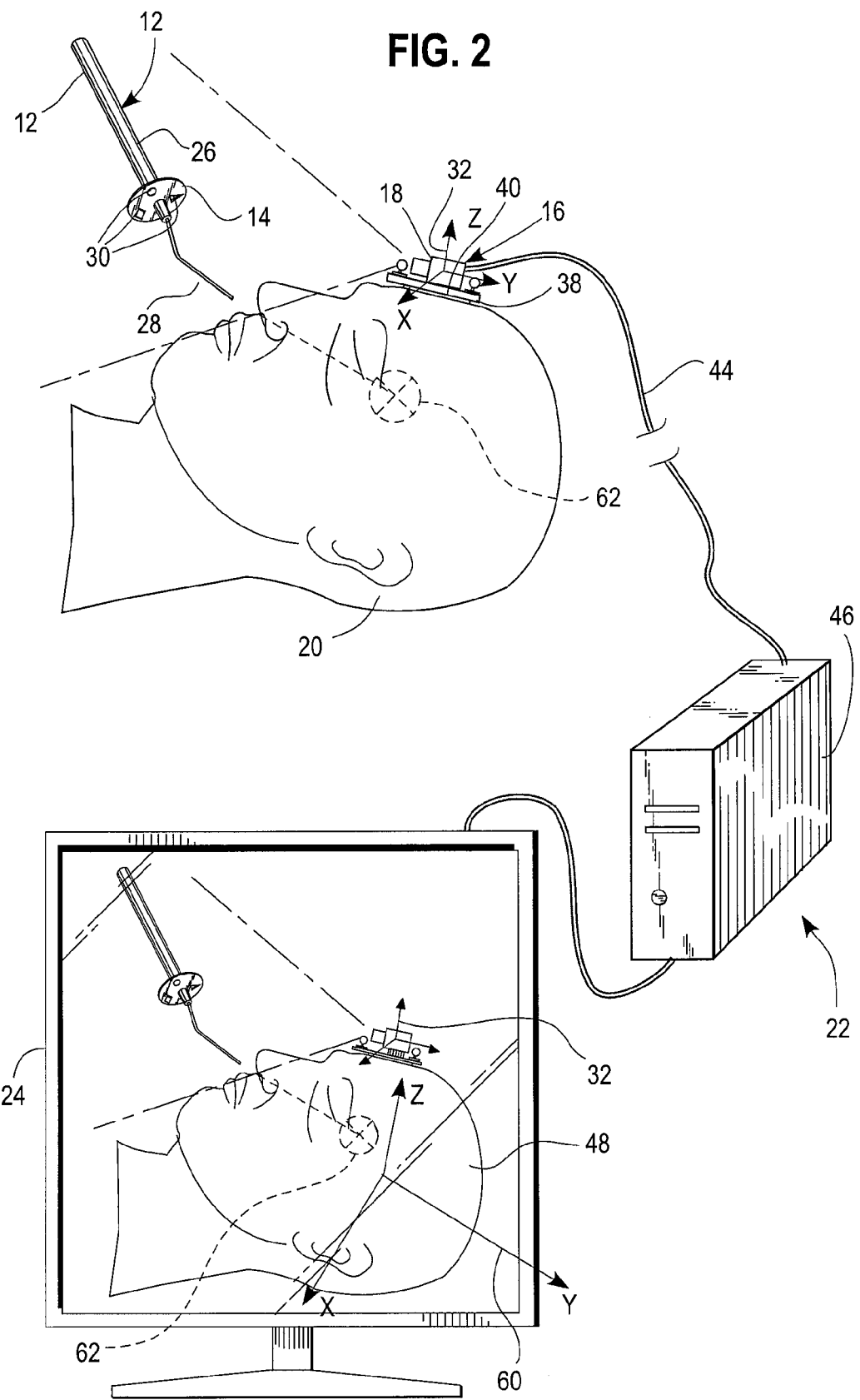
FIG. 2 is another diagrammatic depiction of the surgical navigation system as used during a surgical procedure.

Turning now to the drawings, a preferred embodiment of a navigation system 10 for providing navigation during surgery is shown in FIGS. 1 and 2. The navigation system 10 includes a surgical tool 12 having a tracking element 14 attached thereto, a camera assembly 16 having a surgical navigation camera 18 adapted to be fixedly attached to a patient 20, and a computer processing unit 22 for processing images from the camera 18 and displaying the surgical tool 12 in registration with a scan image of the patient on a display device 24.

The surgical tool 12 may be any tool used during surgery that can be manipulated and arranged in a manner consistent with the purposes, functionality, and methods described herein. In FIGS. 1 and 2, the surgical tool 12 is shown, for example, as a probe having a handle 26 and a tip 28 for insertion into an incision or orifice of the body of a patient 20. Preferably, the surgical tool 12 has a known, pre-identified form factor, that is, the shape, size, and other spatial aspects of interest, such as an axis of the tool tip 28, which is stored in a database that may be accessed by the computer processing unit as described hereinafter. Alternatively, the form factor of the surgical tool 12 may be partially or completely unknown at the start of the procedure, in which case the surgical tool 12 may be identified and/or calibrated in additional steps and such information written to the database. It is generally contemplated that the type of surgical tools most readily adapted for use with the navigation system 10 are hand held tools, but the disclosure is not so limited, as it is clear that almost any type of tool that might be viewed by the camera 18 during a surgical procedure could be adapted for use with the navigation system 10.

The tracking element 14 includes an optical pattern that is readable by the camera and adapted to be processed by a digital image recognition computer program suitable for the uses and purposes described herein. The optical pattern is in a known, fixed position with respect to the tool tip 28, such that the position of the tool tip 28 can be determined from a two-dimensional image of the tracking element 14 taken by the camera 18. The optical pattern comprises passive markers, such as colored ink markings. As used herein, the term "position" means spatial information regarding both the orientation of an object and location or distance of the object from a given point. As shown in FIGS. 1 and 2, one possible optical pattern includes optical navigation markers 30 that can be viewed by the camera 18 and sensed by a digital image recognition program employed by the computer processing unit 22. The tracking element 14 is located where the optical navigation markers 30 will be visible to the camera 18 during normal planned usage of the surgical tool 12 during a given surgical procedure. Preferably, the position of the tracking element 14 on the surgical tool 12 is pre-defined and stored in the database. The tracking element 14 is dimensionally stable. In the present example, the tracking element 14 comprises a rigid or resilient substrate, such as a piece of plastic, cardboard, or metal, that is attached to the surgical tool 12 in a fixed or stable location between the handle 26 and the tool tip 28, preferably near the tool tip 28, with the optical navigation markers 30 oriented facing toward the tool tip 28 in order to be in position to be viewed by the camera 18 while inserting the tool tip 28 into, for example, the patient's nasal passageways to perform the surgical operation. This position of the tracking element 14 avoids disruptions of the line-of-sight between the camera 18 and the tracking element 14 during relevant times in the surgical procedure. The tracking element 14 may be permanently attached to the surgical tool 12 or may be removable and re-attachable, preferably in a pre-selected position. The optical navigation markers 30 on the tracking element 14 comprise a set of shapes and/or colors that can uniquely identify the position and/or identity of the surgical tool 12 when viewed from any viewing angle by the camera 18. For example, the optical navigation markers 30 have three separate shapes in pre-selected positions on the substrate, including a triangle, a square, and a circle, and each optical navigation marker 30 has a different color. The optical navigation markers 30 could take other shapes and/or colors that are able to uniquely identify the position of the tracking element in a two-dimensional image thereof, such as and without limitation, pink hearts, yellow moons, orange stars, and/or green clovers. The optical navigation markers 30 may also have different colors and/or patterns and/or other visually readable cues that are visually readable to the camera 18 and that can be used to uniquely identify the position and/or identity of the surgical tool 12. The optical navigation markers 30 are considered to be passive markers in that they do not emit their own energy. However, in other applications, the tracking element 14 may include active markers, such as LEDs and/or other types of navigation markers that may be sensed by the camera 18. The surgical tool 12 and tracking element 14 are pre-calibrated, whereby the position of the tracking element 14 with respect to the camera assembly 16 may also be automatically identified based on the size and orientation of the optical navigation markers 30 in images obtained from the camera 18. The optical pattern also uniquely identifies the surgical tool 12 with form factor data relative to the surgical tool 12 stored in the database. Specifically, the optical navigation markers 30 provide unique information regarding both position and identity of the surgical tool 12. Alternatively, the optical pattern on the tracking element 14 may be divided into two independent portions, wherein a first portion includes a localization pattern including a set of generic navigation markers 30 that may be used for positional tracking, i.e., localization, of several different tools, and a second portion includes an identification pattern including a separate identification marker that uniquely identifies each surgical tool 12. The identification marker may be any optical identifier, such as a number, bar code, or other symbol that can uniquely identify the identity of the surgical tool 12 to the computer processing unit 22. In this instance, the identification marker is used to access form factor information about the surgical tool 22, and the navigation markers are calibrated with respect to the form factor of that particular surgical tool. In this example, several different tools may use the same localization pattern, and each tool may have a different identification pattern that uniquely identifies the tool.

The surgical tool 12 preferably is not physically connected to the camera assembly 16 or to any other instruments, such as by wires. Thus, for example, the surgical tool 12 can be considered to be wireless because it does not have a wired connection to other components of the navigation system 10. Of course, a surgical tool 12 may include internal wiring for such things as internal circuitry for other structures and/or functions that are contained wholly in the surgical tool. However, the navigation system 10 may have wired connections to other instruments. In addition, the surgical tool 12 with the tracking element 14 with a passive optical pattern may be lighter than a tracking element with LEDs or other heavier structures, and thereby be easier to use during the surgical procedure.

The camera 18 has a completely known focal geometry. The camera 18 is an optical video camera that has a fixed focus lens, which has a focal geometry, including a focal length, focal plane, and focal axis that is fixed with respect to the camera 18 and/or the camera assembly 16 and known to the computer processing unit 22. Thereby, images taken by the camera 18 have a constant relation with respect to the body of the camera 18 and thus a camera coordinate system 32 associated with the camera (also called the "camera space"). Alternatively, the camera 18 may have a changeable focal geometry, such as with a zoom lens, if the focal geometry is determinable and known when tracking.

The camera assembly 16 also includes means for attaching the camera 18 to the patient 20 in a stable, fixed position relative to a surrounding region of the patient 20, and fiducial marks, such as fiducial markers 34, and one or more validation features 36. The camera assembly 16 is preferably small enough to allow for movement and repositioning of the patient 20 while the camera assembly 16 is attached thereto. Further the camera assembly 16 can be packaged and delivered in a sterile condition for immediate use in the surgical procedure without the need to sterilize or drape the camera assembly 16 at the hospital. The camera assembly 16 is also preferably, small, lightweight, and relatively inexpensive so as to be suitable for single use and thereby render cumbersome reprocessing by a hospital unnecessary.

The attachment means may take any form suitable for use to fixedly attach the camera 18 to the patient 20 during a surgical procedure without unduly harming the patient 20 and that allows the camera 18 to be readily removed from the patient 20 at the completion of the surgical procedure. In the examples shown in FIGS. 1, 2, and 4A-4D, the attachment means includes a resilient substrate, such a base plate 38 made of metal or hard plastic plate, which is attached to the camera 18. The camera 18 is attached to the base plate 38 in a fixed known position such that the orientation of the base plate 38 is unchanging with respect to the orientation of the camera 18. The camera 18 is disposed on one side of the base plate 38, such as the top side as shown in FIG. 1, and an adhesive 40 is spread over the opposite side of the base plate 38, such as the bottom side shown in FIG. 1. A protective covering 42, such as a release liner, covers the adhesive 40 to protect the adhesive 40 before it is desired to expose the adhesive 40 for attaching the base plate 38 to the patient 20. The protective covering 42 may be removed just prior to securing the camera assembly 16 to the patient 20. The adhesive 40 is preferably sufficient to securely attach the base plate 38 to the skin of the patient 20 in a fixed manner and also allow removal of the base plate 38 thereafter without causing undue harm to the patient's skin, thereby allowing for non-invasive attachment of the camera assembly 16 to the patient 20. Other means for attaching the camera 18 to the patient may include straps, clamps, pins, screws, clips, and other mechanisms with appropriate functionality. For example, in some instances, the camera 18 without the base plate 38 is attached directly to the patient 20 with adhesive 40, or the camera 18 is clamped to the patient 20 such as with clamps, straps, or any other type of attachment mechanism suitable for use in surgical situations. If desired, invasive attachment mechanisms, such as pins or screws, may be used. Other forms of attachment mechanisms may be particularly advantageous in embodiments where the fiducial markers 34 are not present at all or are integrated with the body of the camera 18 itself.

According to one optional aspect, the fiducial markers 34 are disposed on the base plate 38 in known positions around the camera 18 in sufficient number and location that the fiducial markers 34 may be used to identify the position of the camera 18 and camera coordinate system 32 from an image of the camera assembly 16. In one instance, the camera assembly 16 includes a plurality, preferably three or more, fiducial markers 34, such as metal balls, targets, or other known types of fiducial markers that can be identified in visual light, CT scan, MRI, X-ray, and/or other types of imaging modalities. In another aspect, the fiducial markers 34 may comprise preselected and identifiable shapes and/or objects directly on the body of the camera 18. As shown in FIG. 1, the fiducial markers 34 comprise metal balls, which are visible in most applicable imaging modalities, disposed directly on the top side of the base plate 38 in positions selected to maximize the ability and accuracy of triangulation calculations that will be based thereon, such as nearly an equilateral triangle or a right triangle as shown in FIG. 1. The metal balls are preferably in a fixed, known position with respect to the camera 18 and thus with respect to the focal geometry, the images taken by the camera 18, and the camera coordinate system 32. In this manner, the camera assembly 16 may itself be used for registration of the camera space with a scan image of the patient's body.

The validation feature 36 is an optional feature for validating and/or calibrating the surgical tool 12. As used herein, validation encompasses a procedure that checks whether the geometry, i.e., the form factor, of the surgical tool 12 is within a pre-defined tolerated range of error. For example, a validation of the surgical tool 12 checks whether the tool tip 28 is within a pre-defined tolerated distance of the theoretical position as defined in the database and either accepts or rejects the surgical tool 12. Also as used herein, calibration is a procedure that defines the geometry of the surgical tool 12, and most frequently the position of the tool tip 28, with respect to the tracking element 14. The validation feature 36 may take any suitable form for validating or calibrating the surgical tool 12. In one instance as shown in FIG. 1, the validation feature 36 comprises a known predefined position on the camera assembly 16 such as a point shown or demarcated by an "X" on the base plate 38. The validation feature 36 is located at a fixed, known position on the camera assembly 16 such that the tracking element 14 of the surgical tool 12 is clearly visible to the camera 18 when the tool tip 28 is positioned on the validation feature 36 during a validation or calibration procedure. The validation feature 36 also can be used for calibration and re-calibration of the surgical tool 12. The validation and calibration procedures may be performed by suitable hardware and/or software on the computer processing unit 22 in a manner known and/or readily perceived by a person skilled in the art.

Preferably, the camera 18 and the markers 34 are fixedly attached to the base plate 38 so that the camera 18 and camera coordinate system 32 are in a known, fixed position with respect to the markers 34. In some embodiments, however, the camera 18 is separable from the base plate 38 and can be reassembled only in a predefined spatial relationship thereto. The camera 18 is releasably attached to the base plate 38 with a specially adapted connector, such as a directional quick-release connector, which ensures that the camera 18 can be removed and re-attached in only a single location and orientation. With this feature, the base plate 38 with the fiducial markers 34 can be scanned with the patient, and the camera can be attached thereafter when more convenient. In another embodiment, each fiducial marker 34 is also releasably attached to the base plate 38 by a specially adapted connector, such as a directional quick-release connector or a threaded stud, which ensures that the fiducial markers 34 are reattached in only a single location and/or orientation. This provides the same advantage of having a known spatial relation between the fiducial markers 34 and the camera coordinate system 32, and further may improve ease of handling during imaging and make it easier to maintain sterility during the surgical procedure.

The camera 18 is in communication with the computer processing unit 22 by a data communication link 44 that electronically transmits images obtained from the camera to the computer processor. As shown in FIGS. 1 and 2, the camera assembly 16 includes a hard-wire data communication link 44 for communicating images from the camera 18 to the computer processing unit 22. However, any other types of communication links 44 that are suitable for transmitting the image data from the camera 18 to the computer processing unit 22 may alternatively be used, such as various known wireless data transmission mechanisms, including infra-red, radio frequency, and blue-tooth data communication systems.

The computer processing unit 22 includes a computer processor 46 adapted with hardware and/or software programming that cause the computer processor 46 to read images of the tracking element 14 from the camera 18 and show the position of the surgical tool 12 in registration with a scan image 48 of the patient on the display device 24 from such images. The computer processor 46 may include any hardware and software architecture sufficient to engage in the various processing steps required by the navigation system 10. For example, the computer processor 46 may comprise a single computer, such as a microcomputer or server, or the processor may comprise multiple interconnected data storage and processing units, such as an internet-based processing system located on several disparate but interconnected computers. The scan image 48 may be any image useful to the surgeon to plan and/or execute the surgical procedure, and will generally include such modalities as a CT, ultra-sound, X-ray, MRI, infra-red, visible spectrum, and any other imaging modality suitable for use with surgical procedures. Often, the scan image 48 includes image data relative to subcutaneous structures in the patient's body, such as organs, bones, tumors, cancers, blood clots, and/or other items of interest inside the patient's body.

The computer processor 46 is in communication with the camera 18, the display device 24, and input/output devices 50, such as a keyboard, mouse, digitizer, printer, etc. The computer processor 46 also comprises various hardware and/or software modules or functionalities that adapt the computer processing unit 22 to function as required for the navigation system 10. Thus, the computer processor 46 includes in some manner the following functional components: digital memory that contains the scan image 48 of the patient 20; a database 52 comprising information on the form factor of the surgical tool 12 and tracking elements 14; a digital image recognition module 54 for parsing images received from the camera 18 and identifying various information therefrom, such as the position of the optical navigation markers 30 on the tracking element 14 and location of the tracking element from the camera 18; a registration module 56 for registering the camera 18 and/or the patient 20 with the scan image 48; a tracking module 58 for concatenating position vectors to show an image of a tracked surgical tool 12 in correlation with the scan image 48 on the display device 24 in real time; and a display functionality for displaying the various information on the display device 24. The software and hardware comprising the computer processing unit 22 may be adapted from any such generally available software and hardware, and the present disclosure is not limited to any particular such type of processing capabilities.

The database 52 is associated with the computer processing unit 22 in any suitable manner whereby the computer processor 46 can access the database 52. The database 52 may be any digital database system compatible for interaction with the computer processor 46 and associated hardware and software, and, for example, may be stored on-site or off-site, may be commercially available or proprietary. The database 52 preferably includes information regarding specific surgical tools 12, such as the form factor of a tool and positional and identifying information on the tracking element 14. The database 52 also preferably includes information regarding the camera assembly 16, such as basic form factor information relative to the fiducial markers 34 and the camera space. Of course, the database 52 may include other useful information, such as patient information, information relevant to a surgical procedure to be performed, etc.

The digital image recognition module 54 comprises means for determining a position of the surgical tool 12 with respect to the camera 18, and includes appropriate software and/or hardware algorithms implemented by the computer processor 46 that extract and calculate a position of the tracking element 14 with respect to the camera 18 from an image of the optical navigation markers 30 taken by the camera 18. Many digital image recognition software programs are known and any such program that is able to perform the necessary processes and functionality is sufficient. Preferably, the digital image recognition module 54 is capable of determining the position of the surgical tool 12 from a two-dimensional image of the tracking element 14 visible to the camera 18 by, for example, comparing the image of the optical navigation markers 30 with the form factor data of both the surgical tool 12 and the optical navigation markers 30 available from the database 52. Thus, because the optical navigation markers 30 have a unique two-dimensional image thereof from every possible viewing angle, the position of the tracking element 14 and the surgical tool 12 with respect to the camera 18 can be calculated from a single two-dimensional image thereof, which may be performed in a manner well-known in the art.

The registration module 56 comprises means for registering the camera coordinate system 32 with the scan image coordinate system 60 to be able to show the position of the surgical tool 12 in relation to the patient 20 in correlation with the scan image 48 of the patient on the display device 24. Many suitable registration functions and methods are known in the art and may be adapted for use with the navigation system 10 and methods described herein. Preferably, the registration module 56 is adapted to automatically register the camera 18 with the scan image 48 without any user interaction when the scan image 48 includes the region of interest of the patient and the camera assembly 16 rigidly attached to the patient 20. Alternatively or additionally, the registration module 56 is adapted to facilitate manual registration of the camera 18 with the scan image 48, in which case it may not be necessary for the fiducial markers 34 or the camera 18 to be visible in the scan image 48. Exemplary methods of both automatically and manually registering the camera 18 with the scan image 48 are described in more detail hereinafter.

The tracking module 58 comprises means for determining the position of the surgical tool 12 in relation to the patient 20 and combining such position superimposed and in registration with the scan image 48 of the patient 20 for showing on the display device 24. Any known computer programming capable of making such known mathematical transformations may be used. For example, the tracking module 58 may include a software and/or hardware algorithm that concatenate the position information from the digital image recognition module 54 in combination with form factor information from the database 52 and registration vectors from the registration module 56 to show the surgical tool 12 on the display device 24 in correlation with the scan image 48. Such registration generally is performed by known positional vector concatenation techniques, including positional vectors from the camera 18 to the surgical tool 12, and positional vectors of the camera 18 with respect to points on the patient 20 for example. Such mathematical transformations are well-known in the art and need not be discussed further herein. An advantage of the present navigation system 10 is that the algorithm for performing the concatenation calculations does not have to concatenate a positional vector from a tracking camera to a patient tracker attached to the patient 20 and used solely to identify the position of the patient 20 with respect to the navigation camera. Rather, fixedly attaching the camera assembly 16 directly to the patient 20 effectively eliminates the need for a patient tracker that is separate and independent from the navigation camera because the camera coordinate system 32 is directly correlated with the patient's body in the scan image 48, which reduces the number of coordinate transformations required during navigation and leads to faster performance and higher precision of navigation.

The various computer modules 54, 56, 58 described herein are described as modules only for the sake of simplicity of description. In fact, the functionalities described may be performed in any suitable hardware and/or software architecture capable of determining the orientation of the surgical tool 12 from a two-dimensional image of the tracking element 14 visible to the camera 18 and showing such orientation on the display device 24 in registration with the scan image 48 of the patient 20. In this manner, the computer processing unit 22 with any one of the various modules and/or hardware and software combinations described herein comprises a computer means for tracking the surgical tool, and the aggregate of the software programs comprising the modules 54, 56, 58 may be called simply the navigation software.

The computer processing unit 22 is in communication with the display device 24, which may be any device sufficient to display the position of the surgical tool 12 superimposed with and in correlation with the scan image 48 of the patient 20, such as a computer monitor, television, projector, and/or paper printout from a printer. Preferably, the scan image 48 includes image data portions inside the body of the patient 20 that may not be visible to the surgeon or to the camera 18 so that the display image 48 can show the position of the surgical tool 12 with respect to those portions of the patient's body that are not directly visible to the surgeon. In this manner, the display can display the position of the surgical tool 12 with respect to hidden portions of the patient's body in real time as the surgeon manipulates the surgical tool 12 during the surgical procedure.

Turning now to FIGS. 2 and 3, a general method of using the navigation system 10 includes steps of attaching the camera assembly 16 to the patient 20, registering the camera 18 with the scan image 48 of the patient 20, tracking the position of the surgical tool 12 using the camera 18 and displaying the position of the surgical tool 12 with respect to the patient 20 in correlation with and superimposed over the scan image 48 on the display device 24.

At a block 80, the camera assembly 16 is attached to the patient 20 by the adhesive 40 on the bottom of the base plate 38 in a fixed position such that the camera coordinate system 32 does not move in relation to surrounding areas of the patient 20. Preferably, the camera assembly 16 is small enough to allow the patient 20 to be moved and repositioned by the surgeon as desired while the camera assembly 16 is attached to the patient 20. The camera assembly 16 is fixed to the body with the lens directed to view a region encompassing an expected area of activity during the surgical procedure. For example in an ear, nose, throat surgical procedure, as shown in FIG. 2, it is anticipated that the general activity will include inserting the tool tip 28 through the nasal cavity of the patient 20 to a target location 62 (shown in phantom) in an interior portion of the patient's head. Therefore, the camera assembly 16 is fixedly attached to the skin of the forehead and/or the skull of the patient 20 with the camera lens oriented to have a field of view that encompasses the region above the patient's nose and mouth where the surgical tool 12 is expected to be manipulated during the surgical procedure. When so attached, the camera 18 is fixed relative to the surrounding portions of the patient 20, such as the skull, nasal cavities, and the brain, thereby also fixing the camera coordinate system 32, and preferably the focal geometry, with respect to the surrounding or adjacent areas of the patient's body.

At a block 82, the position of the camera 18 is registered with the position of the patient 20 in a scan image 48. The registration procedure may be performed in any of many different manners and methods known for registering one coordinate system with another. Some specific or preferred automatic and manual methods of conducting such registration are discussed in detail hereinafter. Of particular relevance at this point, however, is that upon registration of the camera space with the scan image space, the relationship between the camera coordinate system 32 and the scan image coordinate system 60 is known sufficiently to be able to calculate and show the position of the surgical tool 12 with respect to the patient 20 in correlation with the scan image 48 on the display 24.

Upon registration of the camera 18 with the scan image 48, the surgical tool 12 with the tracking element 14 is introduced within the field of view of the camera 18, and a block 84 tracks the position of the surgical tool 12 by means of the navigation software, which shows such position on the display monitor 24 in relation to the scan image 48 at block 86. Thus, for example, as a surgeon manipulates the surgical tool 12 through the nasal cavities of the patient 20, the location of the tool tip 28 inside the patient's head is shown on the display monitor 24 in correlated relation to the scan image 48, thereby effectively allowing the surgeon to see on the display device where the surgical tool 12 is in relation to the target location 62 inside the patient 20.

The step of registering the camera with the scan image of the patient performed at block 82 may be performing automatically or it may be performed manually using the registration module 56 of the navigation software.

In FIG. 4, a method of using the navigation system using an automatic registration procedure is shown. In this method, the camera assembly 16 includes fiducial markers 34 that are sufficient to allow the position of the camera 18 to be uniquely identified by the navigation software.

Figure 4A:
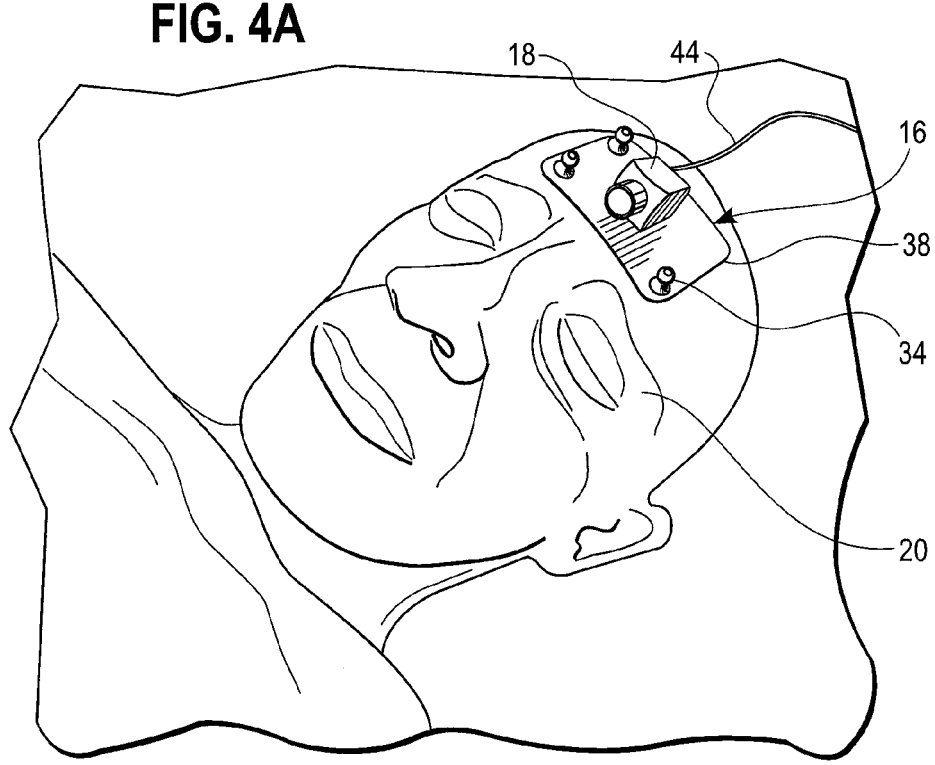
FIGS. 4A-4D illustrate various steps of the method of FIG. 4.

At block 100, the camera assembly 16 is attached to the patient 20 in a fixed position with respect to surrounding portions of the patient's body, as shown in FIG. 4A, with the adhesive 40.

Figure 4B:
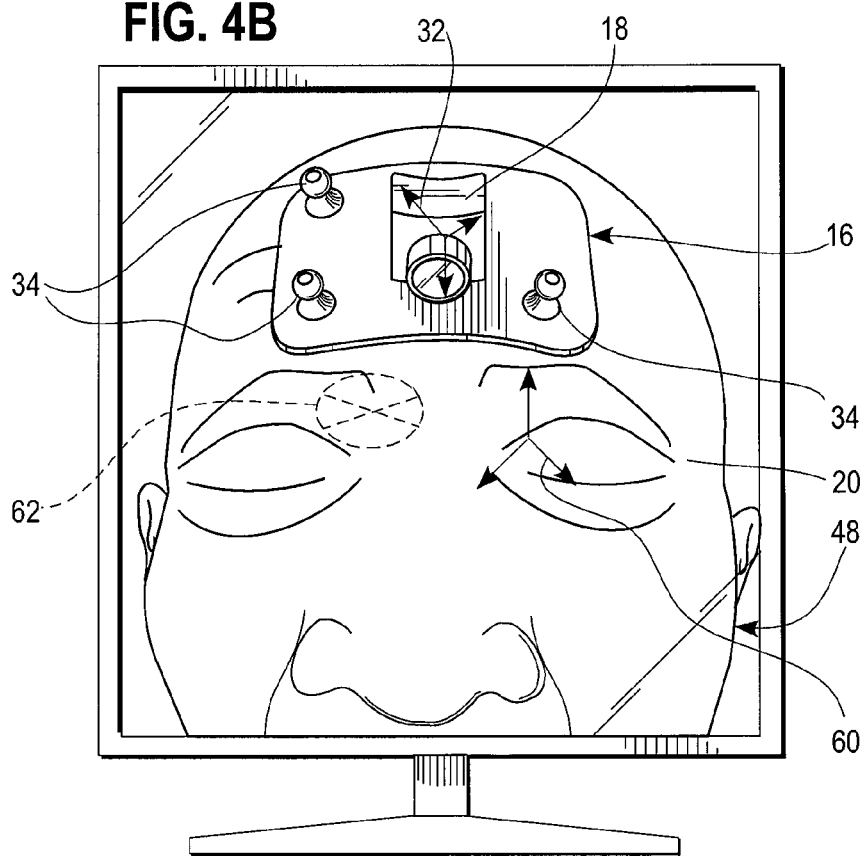

At block 102, a scan image 48 of the patient 20 is obtained with the camera assembly 16 secured to the patient 20, wherein the scan image 48 includes the camera assembly 16 as attached to the patient's body with the fiducial markers 34 visible. An exemplary scan image 48 so obtained is shown in FIG. 4B, which shows the camera assembly 16 attached to the skull of a patient 20 and the fiducial markers 34 of the camera assembly 16 visible in the scan image 48.

At block 104, the navigation software automatically recognizes and identifies the fiducial markers 34 visible in the scan image 48.

At block 106, the navigation software calculates the position of the camera assembly 16 from the position of the fiducial markers 34 in the scan image 48. The position of the fiducial markers 34 with respect to the camera coordinate system 32 and to the focal geometry of the camera 30 is known from form factor information retrieved from the database 52.

At block 108, the navigation software automatically registers the camera space with respect to the position of the patient 20 in the scan image 48 by identifying the position of the camera coordinate system 32 within the scan image 48. Because the patient 20 is fixedly connected to the camera assembly 16, the scan image coordinate system 60 is already directly correlated with the camera coordinates system 32. The registration module 56 automatically performs a coordinate transformation calculation as appropriate and thereby transforms the scan image coordinate system 60 into the camera coordinate system 32 or vice versa. Thereafter, the camera space is registered, or merged, with the scan image space, i.e., the positions of the camera 18 and the scan image 48 of the patient 20 are both known in relation to a single coordinate system, such as the camera coordinate system 32. Upon automatic registration of the camera 18, tracking of the surgical tool 12 is immediately available through the known relationships between the surgical tool 12, the camera coordinate system 32, the scan image coordinate system 60, and form factor information of the surgical tool 12 from the database 52.

Figure 4C:
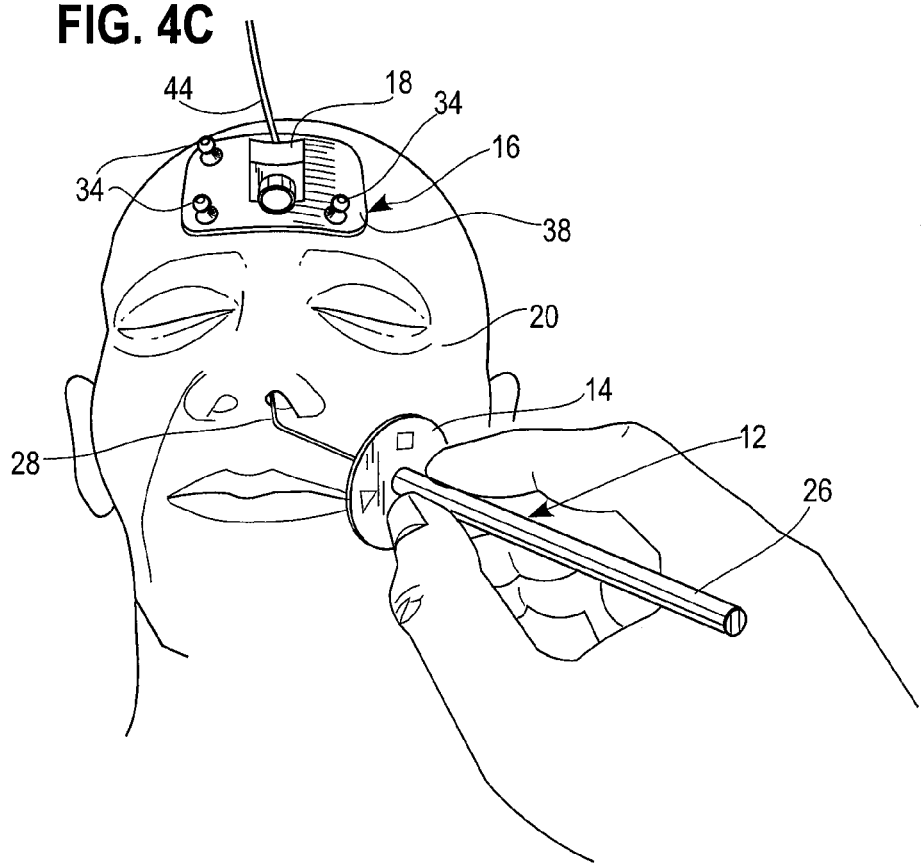
Figure 4D:
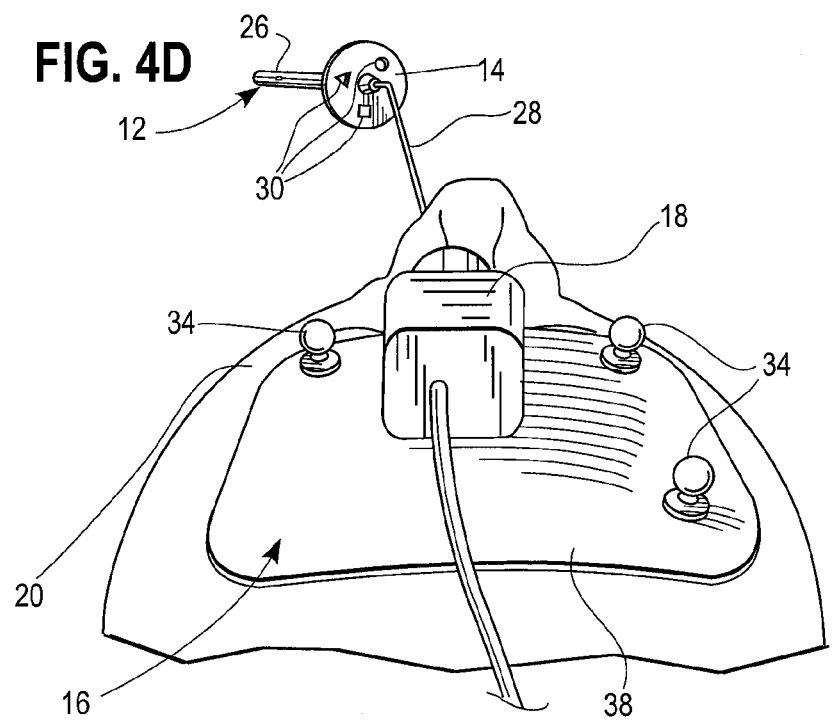

At block 110, the surgical tool 12 is introduced into the view of the camera 18, as shown in FIGS. 4C and 4D. The tracking element 14, as viewed from the camera 18 (shown in FIG. 4D), identifies the surgical tool 12 to the navigation software, which retrieves the relevant form factor information from the database 52 and calculates the position of the surgical tool 12 with respect to the camera coordinate system 32 using the digital image recognition module 54 as discussed previously.

Advantageously, the navigation software does not have to recalculate the transformation between the camera coordinate system 32 and the scan image coordinate system 60 because the camera 18 does not move relative to the patient 20 after the registration procedure until after the surgical procedure is completed. In a preferred embodiment, for example, the scan image 48, which initially is in the scan image coordinate system 60, is transformed into the camera coordinate system 32 a single time during registration and is not recalculated thereafter. Therefore, during navigation, it is only necessary to update the positional vector of the surgical tool 12 relative to the camera coordinate system 32 whenever the surgical tool 12 moves relative to the camera 18. Thus, the navigation system 10 provides a significant reduction of computing resources over prior art navigation systems where the camera space is not fixedly correlated to the patient.

At block 112, a validation procedure is performed to verify whether the surgical tool 12 is within a pre-defined acceptable error range from the form factor information in the database 52. In one method, the tool tip 28 is placed on the validation feature 36 with the optical navigation markers 30 in the field of view of the camera 18. The surgical tool 12 is identified, relevant form factor information for the surgical tool 12 is retrieved from the database 52, and the theoretical position of the tool tip 28 is calculated from the retrieved form factor information. The theoretical position of the tool tip 28 is compared to the actual position of the tool tip 28 on the validation feature 36. If the theoretical position and the actual position of the tool tip 28 are within a pre-defined acceptable error distance of each other, then the surgical tool 12 is verified as acceptable for use in the surgical procedure and control passes to a block 114 for tracking and displaying the surgical tool 12. If the theoretical position and the actual position of the tool tip 28 are not within the pre-defined acceptable error distance of each other, then the surgical tool 12 is rejected for use in the surgical procedure and control passes to block 116.

At block 116, a decision is made whether to replace the surgical tool 12 with a different surgical tool 12 or to calibrate the surgical tool 12. If a new surgical tool 12 is selected, the procedure returns to block 110 and repeats. If, alternatively, it is decided to continue using the same tool 12, the procedure commences to block 118 for performing a calibration procedure.

At block 118, a calibration procedure is performed, wherein the form factor of the surgical tool 12 in relation to the tracking element 14 is calculated and written back to the database 52. In one method, the tool tip 28 is placed on the validation feature 36 with the optical navigation markers 30 in the field of view of the camera 18. The surgical tool 12 is identified by the tracking element 14, and relevant form factor information for the surgical tool 12 is written into the database 52. The position of the tracking element 14 with respect to the actual position of the tool tip 28 on the validation feature 36 is calculated, and that position information is written to the database 52 for use during subsequent tracking. After the surgical tool 12 has been calibrated, the surgical tool 12 preferably is again validated at block 112, and the procedure continues from there. In some circumstances, the calibration procedure may be necessary if there is not sufficient pre-defined form factor information in the database 52, in which case the calibration procedure may be an additional or alternative part of the validation procedure.

After performing the automatic registration, validation, and optional calibration procedures, the surgical procedure commences with complete tracking of the surgical tool 12 from the single camera 18 as the surgical procedure is performed. At block 114, the computer processing unit 22 displays or causes to be displayed the relative position of the surgical tool 12 to the patient 20 in registration with the scan image 48 shown on the display device 24.

Additional surgical tools 12 may be tracked by the camera 18 during the same surgical procedure. Each surgical tool 12 has a tracking element 14 with a unique set of optical navigation markers 30, i.e., having different shapes, colors, and/or spacing, which are stored in the database 52 and uniquely identify each surgical tool 12 to the navigation software. Alternatively, as described above, each tracking element 14 may include the same optical navigation markers 30 for positional tracking, and also include a unique optical identification marker that indicates the identity of the surgical tool 12.

Turning now to FIG. 5, the navigation system 10 may also or alternatively be adapted to manually register the camera 18 with the scan image 48. Although the scan image 48 may be obtained with the camera assembly 16 already attached to the patient 20 as in FIG. 4B, a manual registration procedure is particularly useful when, for example, the camera assembly 16 is not already attached to the patient 20 when the scan image 48 is obtained or where the camera assembly 16 does not include fiducial markers 34. In this method, it is not necessary to be able to identify the fiducial markers 34 in the scan image 48.

In a method of using the navigation system 10 including a manual registration procedure, a scan image of the patient 20 is obtained at a block 120. The scan image is obtained without an image of the camera assembly 16 therein and thus may be taken before the camera 18 is attached to the patient 20.

At block 122, the camera assembly 16 is attached to the body of the patient 20, and the scan image is imported into the computer processing unit 22. Preferably, the camera assembly 16 is attached to a portion of the patient 20 that will not move in relation to the scanned portion of the patient during the surgical procedure.

At block 124, a registration tool is validated and/or calibrated with respect to the position of the camera 18. In one method, the surgical tool 12 is used as a registration tool. Alternatively, a separate tool, such as a pointer (not shown), is used as a registration tool. Validation of the registration tool may be completed in any manner known in the art. Preferably, the validation is performed automatically based on form factor information in the database 52, as described previously with respect to block 112 of FIG. 4. Alternatively or additionally, the registration tool may be calibrated (or recalibrated) at block 124 as described previously with respect to block 118 of FIG. 4. The validation and/or calibration of the registration tool preferably are performed using the validation feature 36 as described previously herein.

At block 126, the registration tool, such as the surgical tool 12, is used to locate points on the body of the patient 20 while tracking the registration tool with the camera 18. The points located may include specific physical landmarks and/or a cloud of points on a surface identifiable in the scan image 48 for performing a registration calculation.

At block 128, the camera 18 is registered with the scan image 48 by matching points located on the body at block 126 to corresponding portions of the scan image 48 of the patient 20 by any method sufficient therefore, such as by performing a point-to-point registration procedure and/or a surface matching registration procedure, and performing appropriate coordinate transformations. In a point-to-point registration procedure, physical landmarks located at block 126 are matched with corresponding structures in the scan image 48. Thereafter, a point-to-point registration procedure is performed to register the camera space with the scan image space by, for example, a point-to-point matching procedure and appropriate coordinate transformations known in the art. In a surface matching registration procedure, the cloud of points located at block 126 is matched to the corresponding surface visible in the scan image 48 by, for example, a surface matching procedure and appropriate coordinate transformations known in the art.

At block 130, if a surgical tool different from the tool used to register the scan image will be used to perform the surgical procedure, the new tool preferably is validated. The validation procedure at block 130 preferably is identical to the validation procedures already described herein and may be omitted if the same surgical tool is used during the procedure that was already validated at block 124 for use to locate the points on the body in block 126.

At block 132, the surgical procedure is started and tracking and displaying of the surgical tool 12 is performed. The steps of tracking the surgical tool 12 and showing the position of the surgical tool 12 on the display device 24 are performed in accordance with the method previously disclosed herein. Thereafter, the computer processing unit 22 shows a representation of the position of the surgical tool 12 in relation to the scan image 48 on the display device 24. In this manner, as the surgical tool 12 is manipulated within the surgical area, the surgeon can see on a video monitor, for example, the position of the surgical tool 12 with respect to interior portions of the patient's head in real time and thereby navigate the surgical tool 12 to a desired location therein, such as the target location 62. Such navigation may be particularly useful when, for example, the target location 62 is planned and identified in the scan image 48 and the navigation system shows where the surgical tool 12 is located in relation to that target location 62.

FIGS. 6 and 7 show another embodiment of the navigation system 10 and a different use location on the patient's body. In FIG. 6, a camera assembly 16 is shown attached to the back of the patient 20 in a fixed position above the patient's spine. The camera assembly 16 is positioned such that the field of view of the camera 18 is pointing upwardly away from the patient's back in order to be able to view the surgical instrument 12 during a spinal surgical procedure. As shown in FIG. 7, the camera assembly 16 is substantially similar to the camera assembly 16 in FIG. 1 in that it includes a camera 18 attached in a fixed orientation and position on a resilient base plate 38, and adhesive 40 carried by the base plate 38 is used to fixedly attach the base plate 38 to the skin of the patient 20. In this embodiment, however, additional attachment means in the form of pins 68 are used to provide additional attachment functionality to the patient 20. The pins 68 extend at an angle through the resilient base plate 38, which may include pre-cut holes 70 adapted for directing the pins in a preselected direction, or the pins 68 may be simply inserted through the resilient base plate 38 without predefined holes therefor. The pins 68 are then driven and/or screwed into a bone or an underlying bone, such as a vertebra 72 as shown in FIG. 7. All the remaining aspects of the camera assembly 16 and method of using the camera assembly 16 are the same as previously described with other embodiments herein. The camera assembly 16 is not limited to use with the spinal cord or attachment to the vertebra 72, but the pins 68 may be used in other locations to attach or to provide additional attachment functionality by screwing the pins 68 into different bones underneath the skin of a patient 20. By using the pins 68, the position of the camera 18 may be fixed in relation to underlying bony structure at locations on the patient 20 where there is substantial soft tissue, such as muscles, tendons, and/or organs underneath the skin, such as at a leg, in the back, or an arm, etc., where such intervening soft tissue may allow an undesirably large amount of movement of the camera 18 on the skin in relation to more fixed bony structures thereunder.

The navigation system 10 in another embodiment may be adapted to include more than one camera 18. The cameras 18 are attached to the patient 20 in a fixed position in the same manner as described previously. Preferably, two or more cameras 18 are also disposed in a fixed, known position in relation to each other, such as by being fixedly attached to the base plate 38 in a known and/or pre-selected orientation. The different cameras 18 may be focused toward different viewing areas around the patient 20 so that the fields of view of the cameras do not overlap or only overlap partially and thereby provide a larger region in which navigation is available. In another embodiment, two spaced-apart cameras 18 are focused on the same viewing area and provide stereo viewing and navigation capabilities, from which navigation by triangulation by known methods is possible. In this embodiment, registration and tracking is preferably performed in accordance with known methods, either as described herein or as known otherwise for stereoscopic navigation processes. Stereoscopic navigation may provide more precise localization tracking with better accuracy for distance perception, and allows for three-dimensional tracking of a single mark in space, such as with a single LED or optical navigation marker 30. Stereoscopic navigation also makes it possible to work with incomplete form factor information of the optical navigation markers.

INDUSTRIAL APPLICABILITY

The navigation system 10 described herein in its various forms is useful for providing navigation information to a surgeon, for example, during an surgical procedure and has several advantages over various surgical navigation systems of the prior art. One advantage is that by securely attaching the camera 18 to the patient 20 in a fixed position, it is possible to merge the camera space with the patient space and thereby eliminate the need for a separate patient tracker as used in many prior art systems. Eliminating the use of a separate patient tracker also eliminates at least one set of positional vectors that must be concatenated in order to track the position of the surgical tool 12 with respect to the patient 20 in a scan image 48 of the patient. Thus, in comparison to prior navigation systems, the present navigation system 10 reduces the amount of computing resources needed to track the surgical tool 12. Another advantage of the navigation system 10 over the prior systems is that separating the camera 18 from the surgical tool 12 allows a single camera 18 to be used to track more than one surgical tool. In addition, a single camera 18 or set of cameras may be used with many different surgical tools at once or in succession if the tracking element 14 includes unique tool identification information readable by the camera 18 and digital image recognition module 54. An additional benefit of the navigation system 10 is that there are no wires that have to be attached to the surgical tool 12 in order to enable the navigation system 10, whereas a system that includes cameras on the tool generally may need wires to provide an acceptable data communication link between the camera and the computer processor. In addition, the navigation system 10 may easily be adapted to navigate surgical tools in many different types of surgical procedures and is not limited to a single surgical procedure or even a predefined set of surgical procedures. Rather, the navigation system 10 may be easily adapted to provide navigation in almost any type of surgical procedure.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved. All patents, patent applications, and other printed publications identified in this foregoing are incorporated by reference in their entireties herein.

I claim:

1. A surgical navigation system comprising:
   a camera attached in a fixed position to a patient with a non-invasive attachment mechanism, wherein the camera has a field of view;
   a surgical tool having a tip and including a tracking element readable by the camera, wherein the tracking element comprises one or more optical navigation markers, and wherein the tracking element is attached to the surgical tool such that the one or more optical navigation markers are oriented facing toward the tip of the surgical tool;
   a computer processing unit comprising means for recognizing the tracking element in an image obtained by the camera and means for tracking the position of the surgical tool; and
   a communication link adapted to transmit images from the camera to the computer processing unit;
   wherein the field of view of the camera is pointing away from the patient.

2. The surgical navigation system of claim 1, wherein the non-invasive attachment mechanism includes an adhesive.

3. The surgical navigation system of claim 2, wherein the camera is configured to be disposed on one side of a resilient base plate and the adhesive is disposed on an opposite side of the base plate.

4. The surgical navigation system of claim 1, wherein the camera further comprises one or more fiducial markers sufficient to define a position of the camera, wherein the fiducial markers are disposed in a known pre-defined spatial relationship with respect to the camera, and wherein the computer processing unit further comprises means for registering the position of the camera from the position of the fiducial markers with an image of a patient.

5. The surgical navigation system of claim 4, wherein the camera has a completely known optical geometry.

6. The surgical navigation system of claim 1, wherein the surgical navigation system comprises a second camera attached in a fixed position to the patient and in communication with the computer processing unit.

7. The surgical navigation system of claim 1, wherein at least one of the optical navigation markers comprises an optical pattern from which the means for recognizing can identify the surgical tool and calculate the position of the surgical tool.

8. The surgical navigation system of claim 7, wherein the optical pattern comprises a localization pattern and an identification pattern.

9. The surgical navigation system of claim 8, further comprising a second surgical tool including a second tracking element, wherein the second tracking element comprises the localization pattern and a different second identification pattern.

10. The surgical navigation system of claim 1, wherein the means for tracking is adapted to track the position of the surgical tool with respect to the patient by directly concatenating a positional vector from the surgical tool to the camera without concatenating a positional vector from the camera to a separate patient tracker.

11. A surgical navigation system comprising:
    a camera assembly comprising a top side and a bottom side;
    a non-invasive attachment means for fixedly attaching the bottom side of the camera assembly to a patient;
    a camera pointing in a direction that is outwardly away from the bottom side of the camera assembly;
    a surgical tool having a tip and including a tracking element readable by the camera, wherein the tracking element comprises one or more optical navigation markers, and wherein the tracking element is attached to the surgical tool such that the one or more optical navigation markers are oriented facing toward the tip of the surgical tool; and a computer processing unit comprising means for determining a position of the surgical tool relative to the camera from an image obtained by the camera that includes the tracking element.

12. The surgical navigation system of claim 11, wherein the image plane of the camera is substantially parallel to the top side of the camera assembly.

13. A surgical navigation system comprising:

a camera capable of being attached in a fixed position to a patient, wherein the camera has a field of view;

a surgical tool having a tip and including a tracking element readable by the camera, wherein the tracking element comprises one or more optical navigation markers, and wherein the tracking element is attached to the surgical tool such that the one or more optical navigation markers are oriented facing toward the tip of the surgical tool;

a computer processing unit comprising an image recognition module for recognizing the one or more optical navigation markers in an image obtained by the camera and a tracking module for tracking the position of the surgical tool; and a communication link adapted to transmit images from the camera to the computer processing unit.

14. The surgical navigation system of claim 13, wherein the one or more optical navigation markers comprise passive navigation markers.

15. The surgical navigation system of claim 13, wherein the tracking element is dimensionally stable.

16. The surgical navigation system of claim 13, further comprising a pin capable of attaching the camera to a bony structure of the patient.

17. The surgical navigation system of claim 13, further comprising a non-invasive attachment mechanism capable of attaching the camera to the patient in a fixed position.

18. The surgical navigation system of claim 17, wherein the non-invasive attachment mechanism includes an adhesive.

19. The surgical navigation system of claim 18, wherein the camera is configured to be disposed on one side of a resilient base plate and the adhesive is disposed on an opposite side of the base plate.

20. The surgical navigation system of claim 13, further comprising one or more fiducial markers sufficient to define a position of the camera, wherein the fiducial markers are disposed in a known pre-defined spatial relationship with respect to the camera, and wherein the computer processing unit further comprises a registration module for registering the position of the camera from the position of the fiducial markers with an image of a patient.

21. The surgical navigation system of claim 20, wherein the camera has a known optical geometry.

22. The surgical navigation system of claim 13, further comprising a second camera capable of being attached in a fixed position to the patient and in communication with the computer processing unit.

23. The surgical navigation system of claim 13, wherein at least one of the optical navigation markers comprises an optical pattern from which the image recognition module can identify the surgical tool and calculate the position of the surgical tool.

24. The surgical navigation system of claim 23, wherein the optical pattern comprises a localization pattern and a first identification pattern.

25. The surgical navigation system of claim 24, further comprising a second surgical tool including a second tracking element, wherein the second tracking element comprises the localization pattern and a second identification pattern, wherein the first identification pattern is different from the second identification pattern.

26. The surgical navigation system of claim 13, wherein the tracking module is adapted to track the position of the surgical tool with respect to the patient by directly concatenating a positional vector from the surgical tool to the camera without concatenating a positional vector from the camera to a separate patient tracker.

* * * * *